United States Patent [19]
Fraefel et al.

[11] Patent Number: 5,998,208
[45] Date of Patent: Dec. 7, 1999

[54] HELPER VIRUS-FREE HERPESVIRUS VECTOR PACKAGING SYSTEM

[75] Inventors: Cornel Fraefel, Brookline; Alfred I. Geller, Boston; Filip Lim, Brookline, all of Mass.

[73] Assignee: Children's Medical Center Corporation, Boston, Mass.

[21] Appl. No.: 09/009,925

[22] Filed: Jan. 21, 1998

Related U.S. Application Data

[63] Continuation of application No. 08/508,088, Jul. 26, 1995, Pat. No. 5,851,826.

[51] Int. Cl.$^6$ ............................. C12Q 1/70; C07H 21/04; C12N 15/11; C12N 15/63
[52] U.S. Cl. ........................... 435/455; 435/6; 435/69.1; 435/375; 435/5; 435/320.1; 536/23.1
[58] Field of Search ............................. 435/6, 69.1, 455, 435/375, 377, 239, 320.1, 235.1; 536/23.1; 514/44

[56] References Cited

U.S. PATENT DOCUMENTS 5,288,641  2/1994  Roizman ............................. 435/320.1

FOREIGN PATENT DOCUMENTS

| | | |
|---|---|---|
| 0 453 242 A1 | 10/1991 | European Pat. Off. . |
| WO 93 08596 | 1/1995 | France . |
| WO 90/09441 | 8/1990 | WIPO . |
| WO 91/02788 | 3/1991 | WIPO . |
| WO 94/21807 | 9/1994 | WIPO . |
| WO 95/06743 | 3/1995 | WIPO . |
| WO 95/20049 | 7/1995 | WIPO . |
| WO 95/27494 | 10/1995 | WIPO . |
| WO 96/04395 | 3/1996 | WIPO . |
| WO 96/26267 | 8/1996 | WIPO . |

OTHER PUBLICATIONS

Verma et al. Gene Therapy—Promises, Problems and Prospects. Nature vol. 389:239–242, Sep. 18, 1997.
Karpati et al. The principles of gene Thereapy for the Nervous System, TINS vol. 19(2):49–54, Jul. 26, 1997.
Orkin et al. Reportand Recomendations of the Panel to Assess the NIH Investment in Research on Gene Therapy, Dec. 7, 1995.
McGuigan, et al., Vaccine, 11:6, 675–678 (1993).
Zhu, et al., J. of Acquired Imm. Deficiencies vol 3, 215–219 (1990).
Lever, et al., J. of Virol. 4085–4087 (1989).
P. J. Bergold, P. Casaccia–Bonnefil, Z. Xiu–Liu, H. J. Federoff, *Proc. Natl. Acad. Sci. U.S.A.* 90, 6165 (1993).
D. S. Battleman, A. I, Geller, M. V. Chao, *J. Neurosci*, 13, 941 (1993).
B. L. Davidson, E. D. Allen, K. F. Kozarsky, J. M. Wilson, B. J. Roessler, *Nat. Genet.* 3,219 (1993).
A. T. Dobson, T. P. Margolis, F. Sedaerati, J. G. Stevens, L. T. Feldman, *Neuron* 5,353 (1990).
G. Le Gal La Salle et al., *Science* 259, 988 (1993).
M. G. Kaplitt et. al., *Nat. Genet.* 8, 148 (1994).
Y. Yang, Q. Li, H. C. J. Ertl, J. M. Wilson, *J. Virol.* 69, 2004 (1995).
Cunningham, et al., *Virology* 197, 116 (1993).
D. Y. Ho and E. S. Mocarski, *Virology* 167, 279 (1988).
D. J. Fink et al., *Hum. Gene Therapy* 3, 11 (1992).
R. R. Spaete and N. Frenkel, *Cell* 30, 285 (1982).
A. D. Kwong and N. Frenkel, *Virology* 142, 421 (1985).
A. I. Geller and X. O. Breakefield, *Science* 241, 1667 (1988).
A. I. Geller and A. Freese, *Proc. Natl. Acad. Sci. U.S.A.* 87, 1149 (1990).
A. I. Geller, K. Keyomarski, J. Bryan, A. B. Pardee, *Proc. Natl. Acad. Sci. U.S.A.* 87, 8950 (1990).
J. G. Stevens, *Curr. Top. Microbiol. Immunol.* 70, 31 (1975).
B. Roizman and F. J. Jenkins, *Science* 229, 1208 (1985).
J. H. Wolfe, S. L. Deshmane, N. W. Fraser, *Nat. Genet.* 1, 372 (1992).
H. J. Federoff, M. D. Geschwind, A. I. Geller, J. A. Kessler, *Proc. Natl. Acad. Sci. U.S.A.* 89, 1636 (1992).
A. I. Geller, M. J. During, J. W. Haycock, A. Freese, R. L. Neve, *Proc. Natl. Acad. Sci. U.S.A.* 90, 7603 (1993).
A. I. Geller, A. Freese, M. J. During, K. L. O'Malley, *J. Neurochem.* 64, 487 (1995).
D. Y. Ho, E. S. Mocarski, R. M. Sapolsky, *Proc. Natl. Acad. Sci. U.S.A.* 90, 3655 (1993).
M. D. Geschwind, J. A. Kessler, A. I. Geller, H. J. Federoff, *Mol. Brain Res.* 24, 327 (1994).
H. Xu, H. Federoff, J. Maragos, L. F. Parada, J. A. Kessler, *Devel. Biol.* 163, 152 (1994).
M. J. During, J. Naegele, K. O'Malley, A. I. Geller, *Science* 266, 1399 (1994).
P. A. Johnson, A. Miyanohara, F. Levine, T. Cahill, T. Friedmann, *J. Virol.* 66, 2952 (1992a).
P. A. Johnson, K. Yoshida, F. H. Gage, T. Friedmann, *Mol. Brain Res.* 12, 95 (1992).
L. H. Nguyen, D. M. Knipe, R. W. Finberg, *J. Virol.* 66, 7067 (1992).
P. A. Johnson, M. J. Wang, T. Friedmann, *J. Virol.* 68, 6347 (1994).
M. J. A. Wood, A. P. Byrnes, D. W. Pfaff, S. D. Rabkin, H. M. Charlton, *Gene Therapy* 1, 283 (1994).
D. Y. Ho et al., *J. Neurosc. Meth.* 57, 205 (1995).
Lieb and Olivo *BioAssay*, 15, 547 (1995).
van Zijl, et al., *J. Virol.* 62, 2191 (1988).

(List continued on next page.)

*Primary Examiner*—Nancy Degen
*Assistant Examiner*—Sean McGarry
*Attorney, Agent, or Firm*—David S. Resnick; Ronald I. Eisenstein; Nixon Peabody LLP

[57] ABSTRACT

We have now discovered a helper virus free herpesvirus packaging system. This system can be used to package a wide range of desired nucleotide segments, preferably a DNA segment, into an empty herpesvirus particle because of the large genomes of herpesviruses. Preferably, the herpesvirus is an alpha herpesvirus. More preferably, the herpesvirus is an alpha herpesvirus such as Varicella-Zoster virus, pseudorabies virus, or a herpes simplex virus such as HSV-1 or HSV-2. Another preferred herpesvirus is Epstein-Barr virus.

9 Claims, 8 Drawing Sheets

OTHER PUBLICATIONS

Cohen, et al., *Proc. Nat'l Acad. Sci.* U.S.A. 90, 7376 (1993).
Tomkinson, et al., *J. Virol.* 67, 7298 (1993).
Markowitz, et al., Virology 167, 400–406 (1988).
Kaplit, et al., Proc. Natl. Acad. Sci. USA vol. 91, pp. 8979–8983 (1994).
T. Friedman, TIG vol. 10, No. 6, (1994).
A. I. Geller, Current Opinion in Genetics and Development 3:81–85 (1993).
Freese, et al., Biochemical Pharmacology, vol. 40, No. 10, pp. 2189–2199 (1990).
Geller, et al., Trends in Neuroscience 14:428–432 (1991).
During, et al., Science, vol. 266, pp. 1399–1403 (1994).
Ferrin, et al., Reports, Dec. 6, 1991 p. 14941497.
Cohen, et al., Proc. Natl. Acad. Sci. USA vol. 90, pp. 7376–7380 (1993).
Heineman, et al., J. of Virol. p. 3317–3323 (1994).

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:1:

```
GGCGGCGGCG GTGGGCCGGG CCTCTGGCGC CGACTCGGGC GGGGGGCTGT CCGGCCAGTC        60
```

(2) INFORMATION FOR SEQ ID NO:2:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:2:

```
CTCAGGTCAG AGATCCAAAC CCTCCGGGGG CGCCCGCGCA CCACCACCGC CCCTCGCCCC        60
```

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:3:

```
TCTGTATCAA CGGTCTGGTC TTGC                                              24
```

(2) INFORMATION FOR SEQ ID NO:4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:4:

```
CATCAGTTGC TGTTGACTGT AGC                                               23
```

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA

```
    (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:5:

GTTGATTGAA CTGCCTGAAC TACC                                              24

(2) INFORMATION FOR SEQ ID NO:6:

(i) SEQUENCE CHARACTERISTICS:
          (A) LENGTH: 23 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

CACTTCAACA TCAACGGTAA TCG                                               23
```

HELPER VIRUS-FREE HERPESVIRUS VECTOR PACKAGING SYSTEM

This application is a continuation of U.S. Ser. No. 08/508,088 filed Jul. 26, 1995, now U.S. Pat. No. 5,851,826.

BACKGROUND OF THE INVENTION

Substantial attention has been given to human gene therapy. This term has been used to describe a wide variety of methods using recombinant biotechnology techniques to deliver a variety of different materials to a cell. Such methods include, for example, the delivery of a gene, antisense DNA or RNA, a gene encoding a cytotoxic agent, etc., by a vector to a mammalian cell, preferably a human cell either in vivo or ex vivo.

Most of the initial work has focused on the use of retroviral vectors to transform these cells. This focus has resulted from the ability of retroviruses to infect cells and have their genetic material integrated into the host cell with high efficiency. The development of a helper virus free packaging system for retrovirus vectors was a key innovation in the development of this vector system for human gene therapy. Retroviral helper virus free packaging systems generally employ the creation of a stable producer cell line that expresses a selected vector. The relatively small size of the retroviral genome, approximately 11 kb, allows for the production of a packaging cell line that synthesizes all the proteins required for viral assembly. Producer lines are made by introducing the retroviral vector into such a packaging cell line.

However, numerous difficulties with retroviruses have been reported. For example, most retroviral vectors are not capable of gene transfer to postmitotic (nondividing) cells and are thus not applicable to the nervous system because most of the cells in the adult nervous system, especially neurons, are quiescent or postmitotic. In addition, outbreaks of wild-type virus from recombinant virus-producing cell lines have also been reported with the vector itself causing a disease.

In light of these difficulties, other vector systems, such as those based on adenovirus, adeno-associated virus, and herpes simplex virus type 1 (HSV-1), are being evaluated for gene transfer into mitotic and non-mitotic cells, especially for use in non-mitotic cells, e.g., neural cells. Each system has limitations: Adenovirus vectors can only support limited long-term (2 months) gene expression, they appear to be gradually lost from neural cells, and moreover, they can cause both cytopathic effects and an immune response (Le Gal La Salle, et al., (1993); Davidson, et al., (1993); Yang, et al., (1995)). Adeno-associated virus vectors cause minimal cytopathic effects and can support at least some gene expression for up to 4 months, but gene transfer is inefficient and these vectors can accept only ~4 kb of foreign DNA (Kaplitt, et al., (1994)). In contrast, vectors based on HSV-1 (Jenkins, et al., (1985); Ho, et al., (1988); Dobson, et al., (1990); Chiocca, et al., (1990); (Fink, et al., (1992); Frenkel, et al., (1982); Kwong, et al., (1985); Geller, et al., (1988); Geller, et al., (1990)) are attractive because HSV-1 can efficiently infect neural cells and can persist indefinitely in neurons (Stevens (1975); Roizman (1981)). Recombinant HSV-1 vectors (Wolfe, et al., (1992)) and HSV-1 plasmid vectors (Federoff, et al., (1992); Battleman, et al., (1993); Bergold, et al., (1993); Geller, et al., (1993); Ho, et al., (1993); Geschwind, et al., (1994); Xu, et al., (1994); Geller, et al., (1995)) have been used to alter neuronal physiology, and HSV-1 plasmid vectors can support some gene expression for up to 1 year (During, et al., (1994)). HSV-1 plasmid vectors contain only ~1% of the 150 kb HSV-1 genome and have been packaged into HSV-1 particles using a helper virus, often a replication-deficient deletion mutant of HSV-1 (Geller, et al., (1990); Lim, et al., (1995)). However, the effectiveness of this vector system has been limited by a number of problems: (i) acute cytopathic effects and an immune response, largely due to gene expression from the helper virus (Johnson, et al., (1992a); Johnson, et al., (1992b); Nguyen, et al., (1992); Johnson, et al., (1994); Wood, et al., (1994); Ho, et al., (1995)) (and in part due to specific proteins in the HSV-1 particle), (ii) potential interactions between the helper virus and endogenous latent viruses, (iii) instability of gene expression (During, et al., (1994)), (iv) potential oncogenesis mediated by the helper virus [as opposed to wild type (wt) HSV-1 which is not known to cause tumors], and (v) reversion of the helper virus to wt HSV-1. The helper virus causes many of these problems and is not required after packaging, however, physical separation of the packaged vector from the helper virus has not yet been achieved. It would be desirable to have a helper virus-free packaging system for herpesvirus vectors. However, heretofore it was believed that development of such a helper virus-free system was unlikely (Lieb and Olivo (1993)).

SUMMARY OF THE INVENTION

We have now discovered a helper virus free herpesvirus packaging system. This system can be used to package a wide range of desired nucleotide segments, preferably a DNA segment, into an empty herpesvirus particle because of the large genomes of herpesviruses.

Preferably, the herpesvirus is an alpha herpesvirus. More preferably, the herpesvirus is an alpha herpesvirus such as Varicella-Zoster virus, pseudorabies virus, or a herpes simplex virus such as HSV-1 or HSV-2. Another preferred herpesvirus is Epstein-Barr virus.

The helper-free virus system for packaging a herpesvirus particle in the absence of a helper virus is based upon using at least one vector which upon delivery into a cell capable of supporting herpesvirus replication will form a DNA segment (or segments) capable expressing sufficient structural herpesvirus proteins so that they are capable of assembly into herpesvirus particles. A single vector or multiple vectors can be used to form the herpesvirus segment (the single or multiple vectors will be referred to as the herpesvirus DNA vector).

For example, sets of cosmids have been isolated which contain overlapping clones that represent the entire genomes of a variety of herpesviruses including Epstein-Barr virus, Varicella-Zoster virus, pseudorabies virus and HSV-1 [See van Zijl, et al, 1988; Cohen, et al., 1993; Tomkinson, et al., 1993; Cunningham, et al., 1993 the contents of which are incorporated herein by reference].

The herpesvirus DNA vector(s) is prepared so that none of the viruses used will contain a functional herpesvirus cleavage-packaging site containing sequence. (This sequence is referred to as the a sequence). This a sequence can be deleted from the herpesvirus DNA vector(s) by any of a variety of techniques well known to the person of ordinary skill in the art. For example, one can simply delete the entire sequence. Alternatively, one can delete a sufficient portion of a sequence to render it incapable of packaging. An alternative strategy is to insert nucleotides into such a site to render it non-functional. Most preferably, one will delete the site entirely to prevent homologous recombination.

A second vector contains a herpesvirus cleavage/ packaging site containing sequence and an origin of DNA replication (ori) which is recognized by the herpesvirus DNA replication proteins and enzymes. This vector permits packaging of desired nucleotide inserts in the absence of helper viruses. This second vector is sometimes referred to as the packaging vector. The origin of DNA replication used is preferably a herpesvirus origin of DNA replication. This second vector is used to package any desired heterologous nucleotide sequence, preferably a DNA sequence, into the particle. Preferably, the packaging vector contains (a) a promoter sequence operably linked to at least one heterologous DNA sequence and (b) at least one sequence sufficient to permit transcription and processing of mRNA, the translation of which results in an expressed protein. Still more preferably, this vector contains an intervening sequence following the promoter sequence. And even more preferably the processing sequence is a polyadenylation sequence. For example, the heterologous sequence can encode any desired protein, preferably a therapeutic protein. It can also encode antisense DNA, RNA or a desired immunogen, such as an antigenic protein. It can encode specific peptide sequence that will generate an immunogenic reaction. Such a peptide sequence are typically at least about 6 amino acids in length.

BRIEF DESCRIPTION OF THE DRAWINGS

In FIG. 1A the HSV-1 genome (top line) is composed of unique long and unique short segments (horizontal lines) which are both flanked by inverted repeats (open rectangles). The IE 1 gene, $ori_S$, and $ori_L$ are shown. The a sequences (solid rectangles), which contain the DNA cleavage/packaging signals, are located at the junction between the long and short segments and at both termini. FIG. 1B is a schematic diagram of the HSV-1 clones from cosmid set C6Δa48Δa (cos6Δa, 28, 14, 56, 48Δa). The deleted a sequences in cos6Δa and cos48Δa are indicated by an X.

DETAILED DESCRIPTION OF THE INVENTION

Figure 1A:
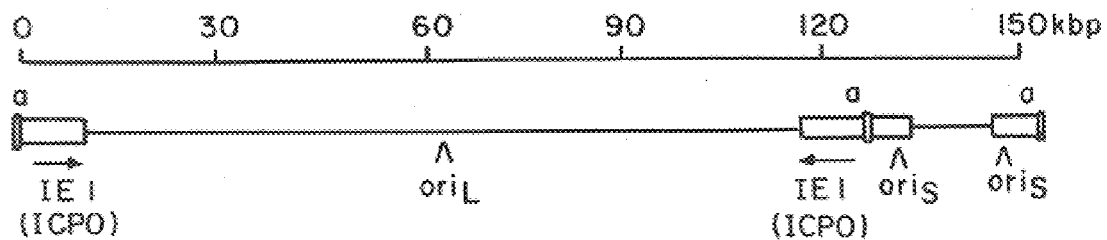
FIGS. 1A and 1B show the development of a helper virus-free packaging system for HSV-1 plasmid vectors.

We have now discovered a helper virus free herpesvirus packaging system. This system can be used to package a wide range of desired nucleotide segments, preferably a DNA segment, into an empty herpesvirus particle because of the large genomes of herpesviruses. For example, the herpes simplex virus (HSV-1) particle, which is approximately 200 mm in diameter, can accommodate ≈150 kb DNA. However, when the vectors are packaged using a helper virus competition between the packaging vector and the helper virus limit the size of the vector to about 15 kb. In contrast, with a helper free system the insert can be substantially larger, preferably the insert can range from just a few kb to about 60 kb, more preferably one would use an insert of about 5 kb–60 kb, still more preferably about 10 kb–50 kb even more preferably, at least about 10–40 kb. As a comparison, the nucleotide insert size limit of adeno-associated virus vectors is ≈4 kb and the present size limit with adenovirus vectors is ≈7 kb. As is known in the art there are genes that are many kb in length, e.g., those encoding Huntington gene products. In addition, the use of promoters and enhancers can also significantly add to the length of an insert. There are also instances were one wishes to insert multiple genes. Accordingly, the system of the present invention provides a significant advantage over currently available vectors by allowing for inserts that can contain a number of promoters and genes.

We have discovered a procedure for preparing empty herpesvirus particles that can be packaged with a desired nucleotide segment in the absence of a helper virus that is widely capable to all herpesvirus. There are over 100 species of herpesvirus. Preferably, the herpesvirus is an alpha herpesvirus. More preferably, the herpesvirus is an alpha herpesvirus such as Varicella-Zoster virus, pseudorabies virus, or a herpes simplex virus such as HSV-1 or HSV-2. Another preferred herpesvirus is Epstein-Barr virus. More preferably, the virus is a herpes simplex virus. Still more preferably, the virus is a HSV-1.

The helper-free virus system for packaging a herpesvirus particle in the absence of a helper virus is based upon using at least one vector which upon delivery into a cell capable of supporting herpesvirus replication will form a DNA segment (or segments) capable of expressing sufficient structural herpesvirus proteins so that they are capable of assembly into herpesvirus particles. A single vector or multiple vectors can be used to form the herpesvirus segment (the single or multiple vectors will be referred to as the herpesvirus DNA vector).

The herpesvirus DNA vector can be constructed using techniques familiar to the skilled artisan. For example, DNA segments encoding the entire genome of a herpesvirus can be divided among a number of vectors capable of carrying large DNA segments, e.g., cosmids (Evans, et al., (1989)), yeast artificial chromosomes (YACS) (Sambrook, et al., (1989)) or *E. coli* F element plasmids (O'Conner, et al., (1989)).

For example, sets of cosmids have been isolated which contain overlapping clones that represent the entire genomes of a variety of herpesviruses including Epstein-Barr virus, Varicella-Zoster virus, pseudorabies virus and HSV-1 [See van Zijl, et al, 1988; Cohen, et al., 1993; Tomkinson, et al., 1993; Cunningham, et al., 1993 the contents of which are incorporated herein by reference].

The herpesvirus DNA vector(s) is prepared so that none of the viruses used will contain a functional herpesvirus cleavage-packaging site containing sequence. (This sequence is referred to as the a sequence). This a sequence can be deleted from the herpesvirus DNA vector(s) by any of a variety of techniques well known to the person of ordinary skill in the art. For example, one can simply delete the entire sequence. Alternatively, one can delete a sufficient portion of a sequence to render it incapable of packaging. An alternative strategy is to insert nucleotides into such a site to render it non-functional. Most preferably, one will delete the site entirely to prevent homologous recombination.

For example, the "a" sequence can be deleted by using techniques known in the art such as the recA-assisted restriction endonuclease cleavage technique [RARE: Ferrin, et al., which is incorporated herein by reference.] Generally one would use two oligonucleotides to form a region of triple stranded DNA at each of two restriction endonuclease sites. The triple stranded DNA is resistant to methylation by methylase. This third strand can subsequently be removed after a methylation reaction. Double stranded DNA is then digested with the appropriate endonuclease which can cleave the DNA only at the sites previously protected from methylation. Accordingly, by appropriate design this method can be used to remove the a sequence from any desired site. Accordingly, the herpesvirus DNA vectors can express the desired herpesvirus proteins, but because the cleavage/packaging site has been removed, the resultant herpesvirus DNA segment will not have packaging sequences that will cause that DNA to be packaged into the herpesvirus particles, and the virus will not be able to replicate and infect other cells.

The core of the herpesvirus particle is formed from a variety of structural genes that create the capsid matrix. It is necessary to have those genes necessary for matrix formation present in a susceptible cell used to prepare particles. Preferably the necessary envelope proteins are also expressed. In addition, there are a number of other proteins present on the surface of a herpesvirus particle. Some of these proteins help mediate viral entry to certain cells. Thus, the inclusion or exclusion of the functional genes encoding these proteins will depend upon the particular use of the particle. This issue will be discussed in greater detail below.

A second vector contains a herpesvirus cleavage/packaging site containing sequence and an origin of DNA replication (ori) which is recognized by the herpesvirus DNA replication proteins and enzymes. This vector permits packaging of desired nucleotide inserts in the absence of helper viruses. This second vector is sometimes referred to as the packaging vector. The origin of DNA replication used is preferably a herpesvirus origin of DNA replication. This second vector is used to package any desired heterologous nucleotide sequence, preferably a DNA sequence, into the particle. Preferably, the packaging vector contains (a) a promoter sequence operably linked to at least one heterologous DNA sequence and (b) at least one sequence sufficient to permit transcription and processing of mRNA, the translation of which results in an expressed protein. Still more preferably, this vector contains an intervening sequence following the promoter sequence. And even more preferably the processing sequence is a polyadenylation sequence. For example, the heterologous sequence can encode any desired protein, preferably a therapeutic protein. It can also encode antisense DNA, RNA or a desired immunogen, such as an antigenic protein. It can encode specific peptide sequence that will generate an immunogenic reaction. Such a peptide sequence are typically at least about 6 amino acids in length.

The heterologous nucleotide sequence can encode a wide variety of proteins such as a therapeutic protein, i.e., one that compensates for an inherited or acquired deficiency. Examples of therapeutic proteins include neurotransmitter biosynthetic enzymes, e.g., tyrosine hydroxylase for the treatment of Parkinson's disease; neurotrophic factors including neurotrophins, e.g., nerve growth factor for the treatment of Alzheimer's disease, one can also use nerve growth factor receptor and the trk receptor; hypoxanthine-guanine porphoribosyl transferase (HGPRT) for the treatment of Lesch Nyhan disease; β-hexosaminadase a chain for the treatment of tay Sachs disease; insulin for the treatment of diabetes. Receptors can also be prepared, e.g. the nerve growth factor receptor, the trk receptor, etc. Because the insert can be large, it is possible to encode a series of different proteins. For example, one can encode a series of proteins that form a receptor-ligand complex.

Other proteins include, for example, signal transduction enzymes, e.g., protein kinase c; transcription factors, e.g., c-fos, NF-Kβ; oncogenes, e.g., erbB, erbB-2/neu, ras; neurotransmitter receptors, e.g., glutamate receptor, dopamine receptor, etc.

The heterologous nucleotide sequence can also encode antisense molecules (DNA or RNA). These molecules can be used to regulate gene expression associated with a particular disease. The antisense molecules are obtained from a nucleotide sequence by reversing the orientation of the coding region with regard to the promoter. Thus, the antisense RNA is complimentary to the corresponding mRNA. For review of antisense science see Green, et al., (1986), which is herein incorporated by reference. The antisense sequence can contain modified sugar phosphate backbones to increase stability and make them less sensitive to RNA sensitivity. Examples of the modifications are described by Rossi, et al., (1991).

The heterologous nucleotide sequence is preferably operably linked to a promoter sequence capable of directing transcription of the sequence in a desired target cell. The promoter can be a promoter such as the HSV-1 IE and IE 4/5 promoters. Promoters capable of directing transcription of the heterologous sequence in a specific target cell can also be used. For example, if the target cell is a neuronal cell, a promoter such as the neuron specific enolase promoter (Forss-Petter, et al., (1986)) can be used. The rat tyrosine hydroxylase (TH) promoter can support cell type specific expression in the midbrain (Song, et al., (1995). Furthermore, the use of inducible promoters or other inducable regulatory sequences, which are well known in the art, in some embodiments are preferred. For example, one could use a tar sequence operably linked to a gene encoding a desired protein if one is targeting an HIV infected cell. In such a system the tat protein produced by such an infected cell will trans activate the expression of the gene operably linked.

In order to minimize the possibility of a recombination event between the packaging vector and the herpesvirus DNA vector generating a wild type herpesvirus it is desirable that the packaging vector has a minimal degree of homology with the at least one herpes-virus DNA vector and/or that the herpesvirus DNA vector does not have at least one functional herpesvirus gene encoding a protein having a cytotoxic or immunogenic function. Thus, preferably one would reduce the sequence overlap between the herpesvirus packaging vector and the herpesvirus DNA vector so that there are no regions of twenty nucleotides or more showing more than forty percent sequence homology with the herpesvirus DNA segment with the exception of the origin of DNA replication (ori) used and any herpesvirus promoters used. Still more preferably, one would use different promoters in these two different vectors. Even more preferably, one would use different origins of DNA replication. These goals can be accomplished by a variety of means known in the art based upon the present disclosure.

For example, if one is using as the herpesvirus, HSV-1, and uses the $ori_s$ in the packaging vector one would delete or substitute a different ori for $ori_s$ in the herpesvirus DNA vector segment. As an alternative to substituting the ori in the herpesvirus vector one might substitute the ori in the packaging vector. More preferably, one would replace the HSV-1 ori with an ori from a different member of the herpesvirus family. For example, the bovine herpesvirus ori is conserved in the core ori region and then diverges and could be used. Similarly, the promoters in the herpesvirus DNA segment could be replaced with other herpesvirus promoters so that they are different than the promoters in the packaging vector. For example, with the HSV-1 $ori_s$ the IE 3 and IE 4/5 promoters are intermingled in the segment before the ori. These promoters could be replaced with other HSV-1 IE promoters such as IE 1 and IE 2. Alternatively, but less preferred is substituting the promoters in the herpesvirus DNA segment. When this is done care must be taken to use a promoter that will provide the appropriate timing for expression of a particular gene. There are additional alternatives for reducing homology between the packaging vector and the herpesvirus vectors such as using a smaller $ori_s$ fragment in the vector. However, the shorter ori fragment can reduce the titer yield. One could use any one of these approaches or a combination thereof to reduce the level of homology.

Alternatively or in combination with the above approach of reducing homology, one can alter the sequence of a gene from the herpesvirus DNA segment so that it does not encode a functional protein. As used herein "functional" means a protein having wild-type activity. For example, one could delete an essential gene or a sufficient portion thereof or a gene necessary for viral DNA replication or cytotoxicity. In addition, one could insert nucleotides altering the reading frame or otherwise preventing expression of a functional protein. For example, with HSV-1 the IE 2 and IE 3 genes are preferred candidates for inactivating an essential gene. This is in part because cell lines that express these genes are known in the art and can be used to obtain expression of the particle without the risk of generating a wild-type virus. For example, E5 cells express IE 3 and 2—2 cells express IE 2. Accordingly, one can routinely express the necessary herpesvirus proteins in desired cell lines.

Depending upon the particle use for these herpesvirus particles one can use known techniques to alter the herpesvirus DNA segment to inactivate genes that encode proteins present in the particle which cause cytopathic effects. For example, inactivating those proteins that affect cellular protein synthesis. In HSV-1 the UL 41 gene products (which are 57 kb and 58 kb) direct both an inhibition of cellular protein synthesis and the degradation of cellular mRNA. [Read, et al., (1993); James, et al., (1995) which are incorporated herein by reference.]

UL 13 encodes a protein kinase which can direct a shut off of cellular protein synthesis. This protein kinase both autophosphorylates and phosphorylates several HSV-1 proteins [Cunningham, et al., (1992); Coulter, et al., (1993)]. Deletion of UL 13 significantly reduces the shut off of cellular protein synthesis indicating that the gene product acts in cooperation with the UL 41 gene product. However, it does not phosphorylate the UL 41 gene product.

One can alter genes that can affect cellular gene expression. For example, with HSV-1 VP 16 increases the activity of IE promoters and may also potentially effect expression of cellular genes.

The UL 48 gene encodes the transactivator. However, the UL 48 gene product itself is essential for HSV-1 particle assembly and this portion of the protein cannot be destroyed but the protein can be altered to destroy or reduce its transactivation activity. [See, Ace, et al., (1988); Ace, et al., (1989)].

The UL 46 gene product increases the transcriptional activity of the UL 48 gene product and the UL 47 gene product decreases the transcriptional activity of the UL 48 gene product. These gene products form a complex with DNA and the UL 48 gene product and a cellular factor (McKnight, et al., (1987); Carpenter, et al., (1991)).

The US 11 gene product associates with a 60 S ribosomal RNA in the nucleolus and inhibits processing of a specific HSV-1 encoded RNA and binds to 60 S ribosomal subunits in the cytoplasm [Roller, (1994)].

There are genes which encode proteins that can affect phosphorylation of cellular proteins. For example, HSV-1 encodes two ser/thr protein kinases. The aforementioned UL 13 and also US 3. Protein phosphorylation can trigger immune reactions and neural cells use signal transduction pathways to process information. Both immune responses and information processing can produce effects that persist long after the HSV-1 particle proteins are degraded. One would preferably minimize these effects by inactivating these proteins using standard techniques based upon the present disclosure. Inactivation can be by mutations to delete the gene encoding the protein, additions of substitutions to inactivate the proteins.

One can also reduce immune responses by inactivating genes encoding non-essential HSV-1 glycoproteins that are present on the surface of the particle. While in some instances it is desirable to mimic the herpes particle as much as possible, in other instances there are many proteins present on the surface of the particle that are not necessary and will only help to generate an immune response. The herpesvirus particles contain many glycoproteins. For example, the HSV-1 particle contains about 12 HSV-1 encoded glycoproteins. Two of these glycoproteins are essential to the HSV-1 lytic cycle: UL 27 and US 6 encode gB and gD which mediate the initial events in infection (e.g., membrane-membrane fusion between the HSV-1 particle and the plasma membrane of the cell). UL 10 encodes gM and deletion mutants in UL 10 grow well in culture fibroblast cells. [MacLean, et al., (1991); Baines, et al., (1991), MacLean, et al., (1993)] UL 43 encodes a membrane associated protein of unknown function but a deletion mutein grows well in cultured fibroblast cells. [MacLean, et al., (1991)]. UL 44 encodes gC and a mutation grows well in cultured fibroblast cells [Hidaka, et al. (1990)]. US 4 encodes gG and a LacZ insertion mutein, which disrupts expression of US 4, and grows well in cultured fibroblast cells [Balan, et al. (1994)]. US 5 encodes gJ and a LacZ insertion mutant, which disrupts expression, and grows well in cultured fibroblast cells [ibid]. US 7 and US 8 encode gI and gE respectively. These two glycoproteins form a complex which function as a receptor for the Fc region in immunoglobulin class G (IgG) and thus partially protect both the HSV-1 particle and infected cells from immune system effector mechanisms (Frank, et al., (1989)). Mutants which disrupt expression of either of these proteins grow well in cultured fibroblast cells. UL 56 encodes a protein contained in the HSV-1 particle which is recognized by IgM and IgG antibodies against HSV-1. Deletion mutants grow well in cultured fibroblast cells and show reduced pathogenicity upon injection into mice (Rosen-Wolff, et al., (1991)). One can inactivate any number of these genes depending upon the manner in which the particle is to be used.

A cell susceptible to infection and DNA replication by a herpesvirus is transfected by the vectors to prepare the viral particle in a helper-virus free system. One can prepare the vectors in vitro, one would then harvest the particles, purify them and inject them by means well known in the art. More preferably one would purify the particles, and then use those to transfect the desired cells.

One can prepare transient or stable cell lines that express the herpesvirus DNA segment by standard techniques based upon the present teaching. For examples, the large fragment from each cosmid used to prepare the herpesvirus DNA segment can be gel purified, packaged into A particles, and propagated as a cosmid in $E.\ coli$. Cosmids lacking the a sequence can be identified using restriction endonuclease analysis. Alternatively, standard mutagenesis techniques such as insertions, deletions or point mutations may be used to delete and/or inactivate the a sequences contained within the herpesvirus DNA segment. Deletions of the a sequence can be selected by screening for clones that have lost the ability to package.

Thereafter, if a stable cell lines is desired one can screen for those cells that have been stably transfected by standard technique.

Such stable herpesvirus DNA cell lines are a preferred source for transfection by the packaging vector. Alternatively, cells can be cotransfected by both the herpesvirus DNA vector and the packaging vector.

The herpesvirus particle of the present invention can be used to deliver heterologous DNA to a target cell. The target cell may be in vivo, in vitro or ex vivo. The target cell can be a dividing or quiescent cell. Quiescent cells include nonmitotic or postmitotic cells. The preferred nonmitotic cell is a glia. The preferred postmitotic cell is a neuron. The target cells also include cells of the nervous system, e.g., neural or neuronal cells.

Introduction of the viral particle carrying the heterologous gene to be delivered to the target cell may be effected by any method known to those of skill in the art. For example, stereotaxic injection can be used to direct the viral particles desired location in the brain. Stereotaxic surgery is performed using standard neurosurgical procedures (Pellegrino and Cushman, (1971)). Additionally, the particles can be delivered by intracerebroventricular ("icv")infusion using a minipump infusion system, such as a SynchroMed Infusion System. A recent method based on bulk flow, termed convection, has also proven effective at delivering large molecules to extended areas of the brain and may be useful in delivering the viral particle to the target cell (Bobo et al., (1994); Morrison et al., (1994)). Other methods can be used including catheters, intravenous, parenteral, intraperitoneal and subcutaneous injection, oral or other known routes of administration.

One would inject a sufficient amount of the viral particles to obtain a serum concentration in the tissue containing the target cell of the therapeutic protein ranging between about 1 pg/ml to 20 µg/ml. More preferably between about 0.1 µg/ml to 10 µg/ml. Still more preferably, between about 0.5 µg/ml to 10 µg/ml.

For example, solid dose forms that can be used for oral administration include capsules, tablets, pills, powders and granules. In such solid dose forms, the active ingredient, i.e., empty virus particle, is mixed with at least one inert carrier such as sucrose, lactose or starch. Such dose forms can also comprise additional substances other than inert diluents, e.g., lubricating agents, such as magnesium stearate. Furthermore, the does forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the virus particle. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml. More preferably, about 3 mg/ml to about 10 mg/ml.

The present invention is further illustrated by the following Examples. These Examples are provided to aid in the understanding of the invention and are not construed as a limitation thereof.

EXAMPLES

EXAMPLE I

Generation of a Helper Virus-free HSV-1 Packaging System

Figure 1B:
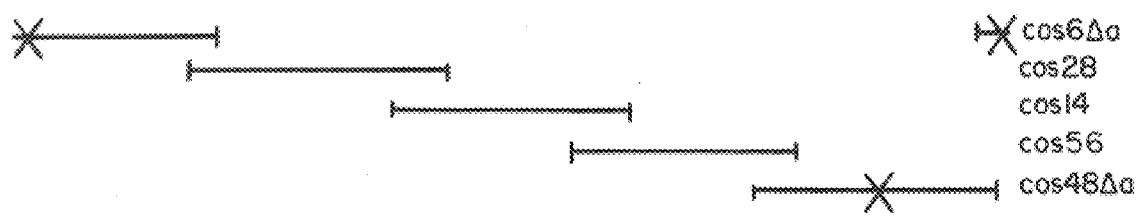

We developed a helper virus-free packaging system by modifying a set of 5 cosmids that represents the HSV-1 genome (cosmid set C) (Cunningham, et al., (1993)): To inhibit virus formation, the a sequence, which contains the DNA cleavage/packaging signal, was deleted from 2 cosmids (cosmid set C6Δa48Δa) (FIG. 1A and 1B).

The a sequences were deleted by selective digestion at 2 HinP1 I sites which flank the a sequences [cos6, nucleotides 783 and 151,436; cos48, nucleotides 125,585 and 126,793 (McGeoch, et al. (1988))] using the recA-assisted restriction endonuclease cleavage technique [Ferrin, et al., (1991)]. Two oligonucleotides were used to form a region of triple-stranded DNA, resistant to methylation by Hha I methylase, at each of the two HinP1 I sites. One oligonucleotide is complementary to nucleotides 753–812 (cos6) and 125, 559–125,618 (cos48) (McGeoch, et al., (1988).

(5'GGCGGCGGCGGTGGGCCGGGCCTCTGGCGC CGACTCGGGCGGGG GGCTGTCCGGCCAGTC3') (SEQ ID NO:1), and the other oligonucleotide is complementary to nucleotides 151,409–151,468 (cos6) and 126,764–126,823 (cos48)

(5'CTCAGGTCAGAGATCCAAACCCTCCGGGGG CGCCCGCGCACCACCACCGCCCCTCGCCCC3') (SEQ ID NO:2).

Ninety ng of each oligonucleotide, 1 μg cosmid DNA, and 10 μg of E. coli recA protein (New England Biolabs) were incubated together for 10 min at 37° C. Ten units Hha I methylase (New England Biolabs) and S-adenosylmethionine (120 μM final concentration) were added and the reaction was incubated for 50 min at 37° C. After heat treatment (65° C., 10 min) to inactivate the Hha I methylase and to dissociate the recA-DNA complexes, the DNA was digested with HinP1 I. The large DNA fragment was isolated by agarose gel electrophoresis, ligated using T4 DNA ligase, and packaged into bacteriophage lambda particles (Gigapack II Plus, Strategene). Cosmids were propagated in E. coli XL1 Blue MR (Stratagene), and cosmids lacking the a sequence were identified by restriction endonuclease analysis. Similar methods have been used to delete the large subunit of ribonucleotide reductase from a cosmid set representing the varicella-zoster virus genome [Heineman, et al., (1994)].

pHSVlac, the plasmid vector used in this example, contains the HSV-1 origin of DNA replication $ori_s$ and an a sequence to support packaging and expresses the E.coli lacZ gene from the HSV-1 immediate-early (IE) 4/5 promoter (Geller, et al., (1988); Geller, et al. (1990)).

Cosmids were digested with Pac I to excise the HSV-1 inserts and purified by phenol extraction. 2—2 cells (Smith, et al., (1992)) were grown in Dulbecco's modified minimal essential medium (DMEM) containing 10% fetal bovine serum (FBS) and plated at a density of $4×10^5$ cells/60 mm tissue culture dish. The following day, the cells were transfected using the lipofectAMINE procedure (GIBCO): 0.4 μg of pHSVlac DNA and 0.4 μg of each cosmid DNA were diluted in 100 μl OPTI-MEM I, mixed with 100 μl OPTI-MEM I containing 12 μl lipofectAMINE, and incubated at room temperature for 45 min before addition of 0.8 ml OPTI-MEM I. The cells were washed once with OPTI-MEM I, the DNA/lipofectAMINE solution was added, and the cells were incubated at 37° C. for 5.5 h. After the cells were washed 3 times with OPTI-MEM I, 3 ml DMEM containing 2% FBS were added, and the cells were incubated at 37° C. for 2.5 days. To harvest pHSVlac particles, the cells were scraped into the medium, the suspension was frozen and thawed 3 times, sonicated, and cell debris were removed by centrifugation (10 min, ~1,400 Xg). 2—2 cells were used because they transfect at a high efficiency; however, this procedure has been successfully performed using either VERO cells or BHK-21 cells, although the titer of pHSVlac was lower.

Following cotransfection of cells with a mixture of cosmid set C6Δa48Δa and pHSVlac, the cosmids directed the packaging of pHSVlac into HSV-1 particles (pHSVlac/helper-free), but no HSV-1 was produced. This result has been repeated in ~200 packaging experiments with cosmid set C6Δa48Δa and pHSVlac.

The properties of pHSVlac stocks obtained using different packaging procedures are set forth in Table I below. pHSVlac was packaged using either the helper virus-free system or using a helper virus, KOS 5dl1.2. The titers of pHSVlac (IVP) were determined using BHK-21 cells and cytochemical staining with X-gal, and the titers of HSV-1 (PFU) were determined using 2—2 cells by standard plaque assays. Expression of the IE 1 gene was detected using an anti-ICP0 antibody. ND=not done.

TABLE I

| Packaging Condition | Vector IVP/ml | Helper virus PFU/ml | Vector/helper IVP/PFU | ICP0 immunoreactivity positive cells/$10^5$ IVP |
|---|---|---|---|---|
| pHSVlac;cos 6Δa, 28, 14, 56, 48Δa(exp.1) | $4.0 × 10^5$ | <1 | $>4.0 × 10^5$ | <1 |
| pHSVlac;cos 6Δa, 28, 14, 56, 48Δa(exp.2) | $2.0 × 10^5$ | <1 | $>2.0 × 10^5$ | <1 |
| pHSVlac;cos 6Δa, 28, 14, 56, 48Δa(exp.3) | $1.5 × 10^5$ | <1 | $>1.5 × 10^5$ | <1 |
| —;cos 6Δa, 28, 14, 56, 48Δa | <1 | <1 | | ND |
| pHSVlac; | <1 | <1 | | ND |
| pHSVlac;cos 6Δa, 28, 14, 56, 48 | $5.2 × 10^5$ | $4.0 × 10^1$ | $1.3 × 10^4$ | ND |
| pHSVlac;cos 6, 28, 14, 56, 48Δa | $7.0 × 10^5$ | $1.4 × 10^2$ | $5.0 × 10^3$ | ND |
| pHSVlac;cos 6, 28, 14, 56, 48 | $7.0 × 10^5$ | $1.6 × 10^3$ | $4.4 × 10^2$ | ND |
| pHSVlac;HSV-1 5dl 1.2 helper virus | $5.9 × 10^6$ | $6.0 × 10^6$ | 0.98 | $1.4 × 10^{4*}$ |

*The sensitivity of the ICP0 antibody was ~14% ($1.4 × 10^4$ ICP0 immunoreactive cells/$9.8 × 10^4$ PFU KOS 5dl 1.2.

Figure 2A:
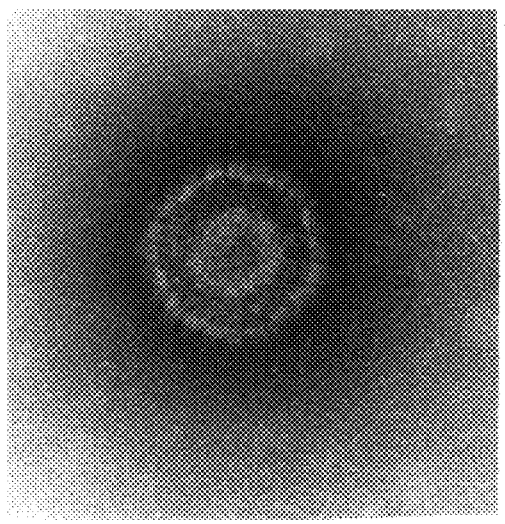
FIGS. 2A and 2B are electron micrographs of pHSVlac/ helper-free showing (2A) cross-sectioned and (2B) intact nucleocapsids. Scale bars, 100 nm.
Figure 2B:
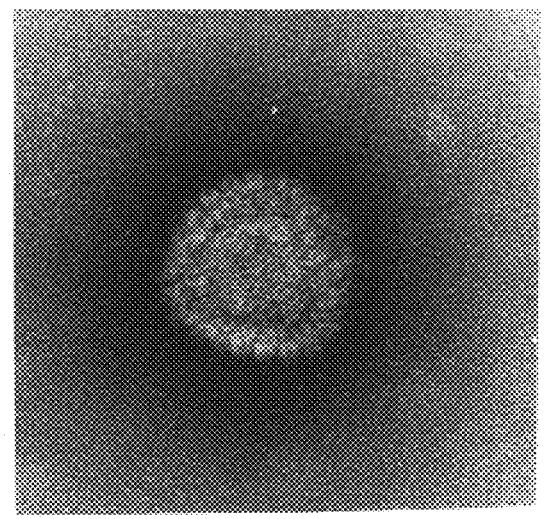

These vector particles were examined by electron microscopy by adsorbing the pHSVlac/helper-free particles onto carbon coated parlodion films. They were then mounted on 300 mesh copper grids, negatively stained for 30 s with 2% Na-phosphotungstic acid (pH 6.6), air dried, and immediately examined at 100 kV using a Philips CM12 electron microscope. Examination of these vector particles by electron microscopy revealed nucleocapsids (FIGS. 2A and 2B) with a structure comparable to wt HSV-1 (Schrag, et al., (1989)).

Transfections performed with only cosmid set C6Δa48Δa or only pHSVlac produced neither packaged vector nor HSV-1, whereas transfections performed with pHSVlac and a cosmid set containing either only 1 a sequence or 2 a sequences (unmodified cosmid set C) supported both the packaging of vector and the formation of HSV-1.

Because of the limited sequence homology between pHSVlac and both cos6Δa and cos48Δa (1.05 kb containing the $ori_s$ and the IE 4/5 promoter), homologous recombination between pHSVlac and either cosmid could generate a fragment of the HSV-1 genome that contains both elements required for packaging ($ori_s$ and an a sequence). However, to be replicated and packaged, such a DNA molecule would have to be circularized, and to generate a complete circular HSV-1 genome, a minimum of 6 recombination events would be required.

The probability of generating infectious HSV-1 might be further reduced by eliminating any sequence homology between HSV-1 plasmid vectors and cosmid set C6Δa48Δa; production of infectious HSV-1 would then require an illegitimate recombination event. Furthermore, deletion of an essential gene [e.g. IE 2 (21)] from cosmid set C6Δa48Δa may ensure that if any helper virus was produced, it is unlikely to be wt HSV-1.

To determine whether any recombinants between pHSV-lac and either cosmid were packaged, we performed immunocytochemistry using an anti-ICP0 antibody. One day after infection, VERO cells were fixed with 4% paraformaldehyde and then incubated overnight with a mouse anti-ICP0 antibody (1:1000 dilution of ascites) [Everett, et al., (1993)]. Immunoreactivity was visualized using an alkaline phosphatase-conjugated goat anti-mouse IgG antibody (1:2000 dilution) (Boehringer Mannheim) and the BCIP/NBT substrate (Sigma).

ICP0 is encoded by the IE 1 gene present in both cos6Δa and cos48Δa (FIG. 1A and 1B) and is absent from HSV-1 particles. ICP0 immunoreactivity was not detected in cells infected with pHSVlac/helper-free (Table I) but was observed in the nuclei of cells infected with pHSVlac packaged using a DNA replication-deficient helper virus (pHSVlac/helper), produced as discussed above. In contrast, HSV-1 particle immunoreactivity was observed following infection with either pHSVlac/helper-free or pHSVlac/helper (not shown).

To produce the DNA replication-deficient helper virus (pHSVlac/helper), pHSVlac was packaged by established procedures (Geller, et al., (1990); Lim, et al., (1995)) using the IE 2 deletion mutant HSV-1 KOS 5dl1.2 (Sacks, et al., (1987)), and 2—2 cells (Smith, et al., (1992)). This helper virus caused cytopathic effects similar to IE 3 deletion mutants, and the reversion frequency to wt HSV-1 was $<10^{-7}$ (F. Lim, unpublished material).

EXAMPLE II

IN VITRO GENE TRANSFER

Before use in gene transfer experiments, pHSVlac stocks were purified and concentrated (Lim, et al., (1995)) to achieve a titer of at least $1 \times 10^7$ infectious vector particles (IVP) per ml. Cultured rat cerebral cortical cells (Choi, et al., (1987)) were infected with pHSVlac/helper-free or pHSVlac/helper and stained with X-gal (Emson, et al., (1990); Smith, et al., (1995)) after 2, 4, or 8 days. Cultures infected with pHSVlac/helper displayed a gradual decline in the number of β-galactosidase positive cells (FIG. 2, A, B, and G) during this time period. In contrast, following infection with pHSVlac/helper-free, the number of β-galactosidase positive cells remained relatively constant (FIG. 2, C, D, and G), and the positive cells displayed either neuronal or glial morphology (FIG. 2, E and F). Cytopathic effects were quantified by measuring the release of lactate dehydroxygenase (LDH) activity from the cells into the culture medium from days 7 to 8 after gene transfer (Koh, et al., (1987)). pHSVlac/helper caused a ~2-fold increase in LDH release compared to mock infected cultures, whereas pHSVlac/helper-free did not significantly change LDH release (not shown).

EXAMPLE III

IN VIVO GENE TRANSFER

Equal amounts ($9 \times 10^3$ IVP) of either pHSVlac/helper or pHSVlac/helper-free, or phosphate buffered saline (PBS), were stereotaxically injected into the right midbrain (MB) and the left striatum (ST) of adult rats. Virus stocks were delivered by stereotaxic injection (3 μl/site over 10 min) into the right MB (AP 3.5, ML 4.0, DV 6.8; 20° angle for needle towards midline) and the left ST (AP 0.5, ML 0.0, DV 6.0) of male Sprague Dawley rats (100–125 gm). The coordinates indicate millimeters relative to Bregma and Bregma-Lambda [Paxinos, et al., (1986)]. Four days or 1 month later, the rats were anesthetized with chloral hydrate (400 mg/kg, ip) and transcardially perfused with 50 ml of PBS followed by 200 ml of 4% paraformaldehyde in PBS. The brains were cryoprotected, 30 μm coronal sections were cut using a freezing microtome and stored in PBS at 4° C. Sections were stained with either cresyl violet or X-gal (Emson, et al., (1990); Smith, et al., (1995)), and cell counts were performed under 30× magnification.

Figure 3A:
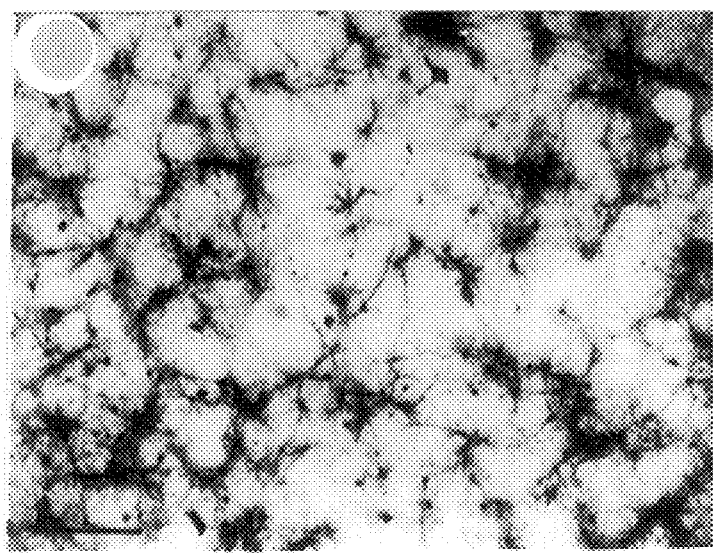
FIGS. 3A, 3B, 3C, 3D, 3E and 3F illustrate gene transfer into cultured cortical cells using pHSVlac/helper-free or pHSVlac/helper. Photomicrographs of β-galactosidase positive cells are shown: pHSVlac/helper, (3A) 2 days or (3B) 8 days after gene transfer; pHSVlac/helper-free, (3C) 2 days, (3D) 8 days, (3E, 3F) 2 days at high magnification showing either neuronal or glial morphology, respectively. Scale bars: 500 μm (A–D), 50 μm (E, F).
Figure 3B:
Figure 3C:
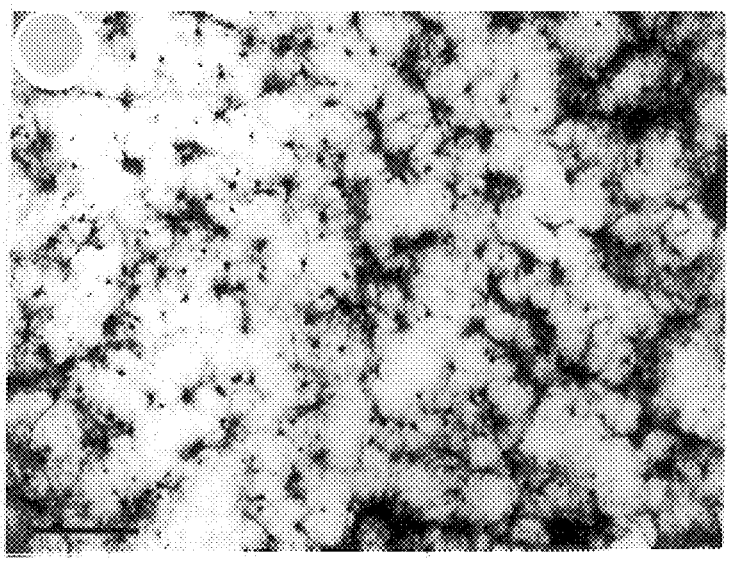
Figure 3D:
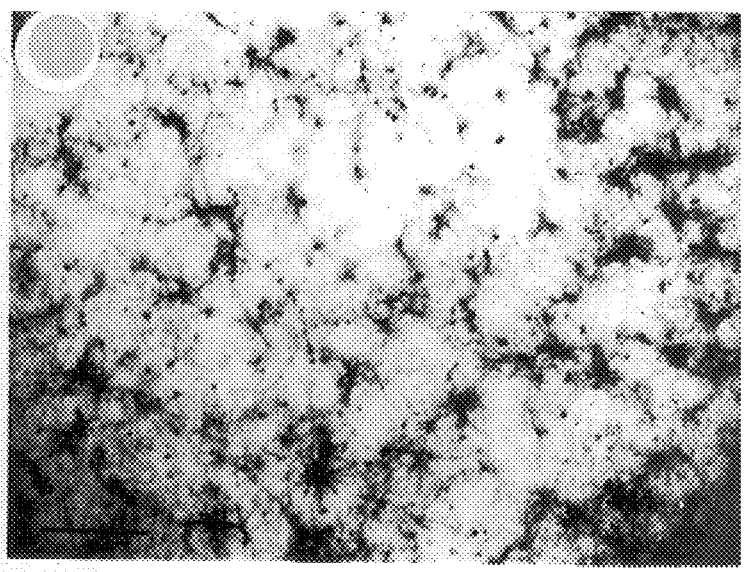
Figure 3E:
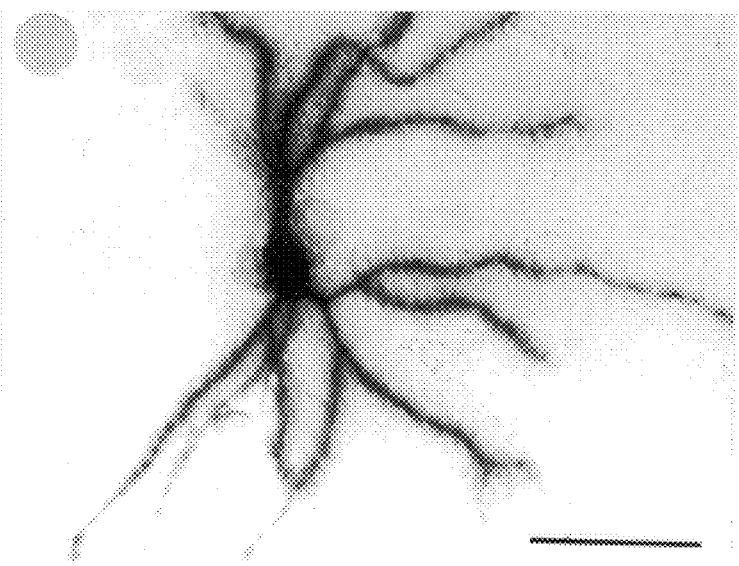
Figure 3F:
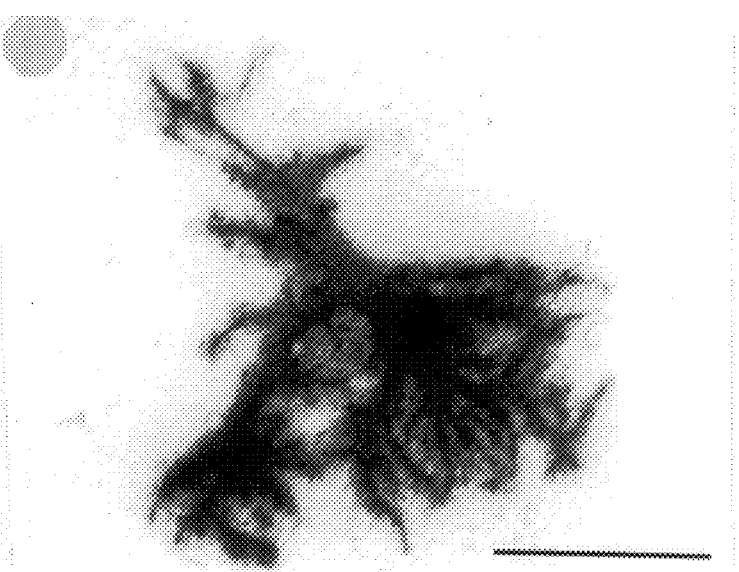
Figure 4:
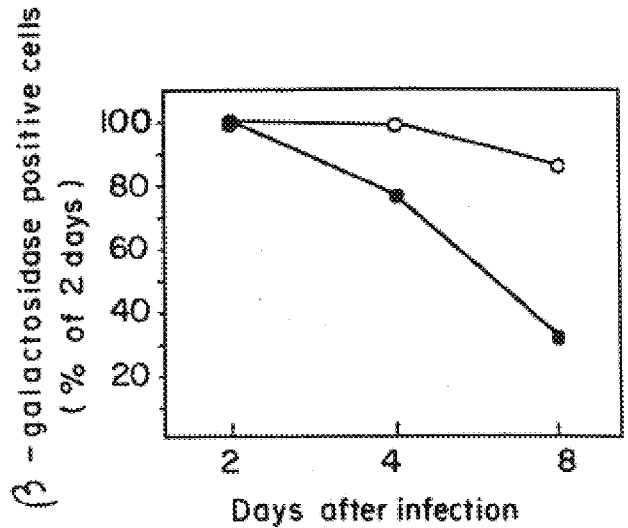
FIG. 4 illustrates the quantification of the number of β-galactosidase positive cells at various times after gene transfer with either pHSVlac/helper-free (open circles) or pHSVlac/helper (closed circles). The data are expressed as the % of β-galactosidase positive cells observed at 2 days after gene transfer (~1,200) and the results are the means of 3 experiments.

Four days after injection of pHSVlac/helper, cresyl violet staining revealed many infiltrating cells and considerable cell damage proximal to the injection sites (FIGS., 3A and Table II). In contrast, pHSVlac/helper-free caused minimal cell infiltration or cell damage, and the injection sites appeared similar to those obtained using PBS (FIG. 3, B and C; Table II). Perhaps due to the reduced cytotoxicity, pHSVlac/helper-free produced more β-galactosidase positive cells than pHSVlac/helper (FIG. 3, D and E; Table 11). Injection of ~3-fold more pHSVlac/helper-free ($3 \times 10^4$ IVP) resulted in an approximately proportional increase in the number of β-galactosidase positive cells with minimal cell damage (FIG. 3F). At 1 month after gene transfer, the number of β-galactosidase positive cells had significantly declined: pHSVlac/helper-free produced an average of ~5% (MB) and ~2% (ST) of the number of β-galactosidase positive cells observed at 4 days, and pHSVlac/helper produced no positive cells in either area (2 rats/group). At both 4 days and 1 month after injection of pHSVlac/helper-free, many of the β-galactosidase positive cells displayed neural morphology (FIG. 3, G and H).

Table II set forth below illustrates the efficiency of gene transfer and persistence of pHSVlac DNA in the brain. In Table II the average number of β-galactosidase positive cells and the average area of cell infiltration were determined at 4 days after gene transfer into the right MB and the left ST (25) (3 rats/group).

TABLE II

| Condition | pHSVlac IVP | Average X-gal positive cells | | Efficiency of gene transfer (%)* | | Area of cell infiltration (mm²) | |
|---|---|---|---|---|---|---|---|
| | | MB | ST | MB | ST | MB | ST |
| helper | $9 \times 10^3$ | 113 | 140 | 1.3 | 1.6 | 1.0 | 1.6 |
| helper-free | $9 \times 10^3$ | 124 | 407 | 1.4 | 4.5 | 0.2 | 0.6 |
| PBS | — | 0 | 0 | — | — | 0.1 | 0.6 |

*The efficiency of gene transfer (%) is the average number of β-galactosidase positive cells/IVP of pHSVlac, multiplied by 100.

DNA was extracted from brain sections adjacent to those used for staining and was subjected to polymerase chain reaction (PCR) analysis as follows: 0.5 mg tissue/µl [Higuchi, (1989)], and aliquots were subjected to nested PCR using primers (5 pmoles) derived from the lacZ gene [(Kalnin, et al., (1983))]. First reaction: 10 ng DNA in 100 µl; primers, nucleotides 1,802–1,826 (5'TCTGTATCAACGGTCTGGTCTTGC3') (SEQ ID NO:3) and complementary to nucleotides 2,882–2,905 (5'CATCAGTTGCTGTTGACTGTAGC3') (SEQ ID NO:4); 25 cycles; 94° C., 1 min; 50° C., 1 min; 72° C., 4 min. Second reaction: 2 µl of the first reaction in 100 µl; primers, nucleotides 2,034–2,057 (5'GTTGATTGAACTGCCTGAACTACC3') (SEQ ID NO:5) and complementary to nucleotides 2,594–2,616 (5'CACTTCAACATCAACGGTAATCG3') (SEQ ID NO:6); 40 cycles; 94° C., 1 min; 55° C., 1 min; 72° C., 4 min. The reaction products were electrophoresed on a 1.2% agarose gel.

Figure 6:
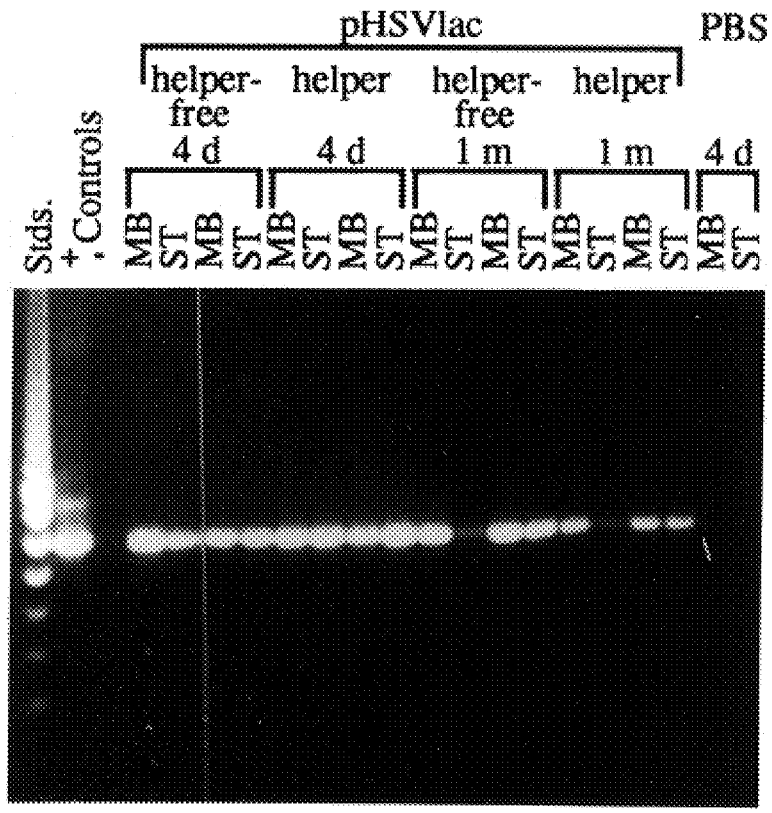
FIG. 6 illustrates the efficiency of gene transfer and persistence of pHSVlac DNA in the brain. PCR analysis of pHSVlac DNA at 4 days or 1 month after injection of either pHSVlac/helper-free or pHSVlac/helper (2 rats at each time point), or PBS (1 rat, 4 days). Control reactions contained either (+) pHSVlac DNA purified from *E. coli* or (−) no DNA. Stds., 100 bp ladder. The 583 bp reaction product is indicated (arrow).
Figure 5:
FIGS. 5A, 5B, 5C, 5D, 5E, 5F, 5G and 5H are photomicrographs showing cell infiltration and β-galactosidase positive cells following gene transfer into the rat brain. Cresyl violet staining of the injection site in the MB following delivery of (5A) pHSVlac/helper, (5B) pHSVlac/helper-free, or (5C) PBS. β-galactosidase positive cells adjacent to the injection site in the ST using (5D) pHSVlac/helper or (5E, 5F) pHSVlac/helper-free. Individual β-galactosidase positive cells in the ST at (5G) 4 days or (5H) 1 month after injection of pHSVlac/helper-free. Scale bars, 50 μm.
Figure 5:
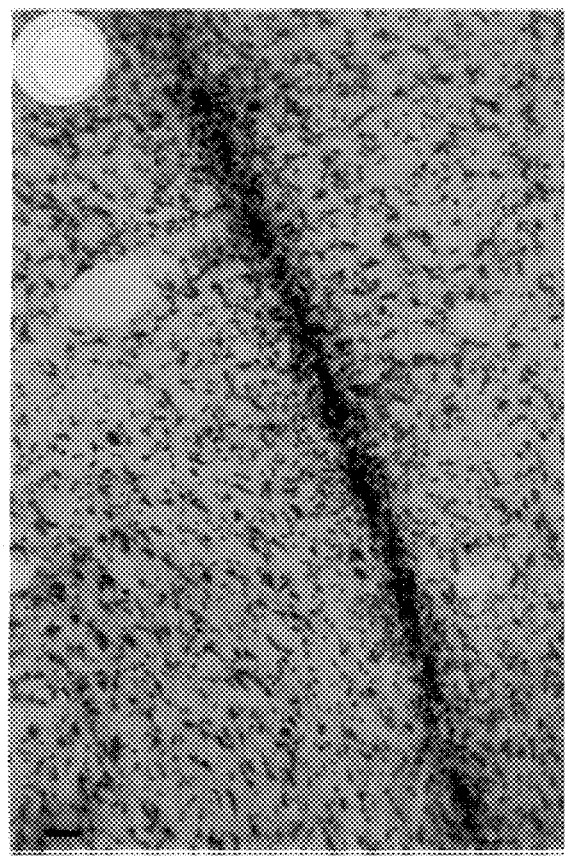
Figure 5C:
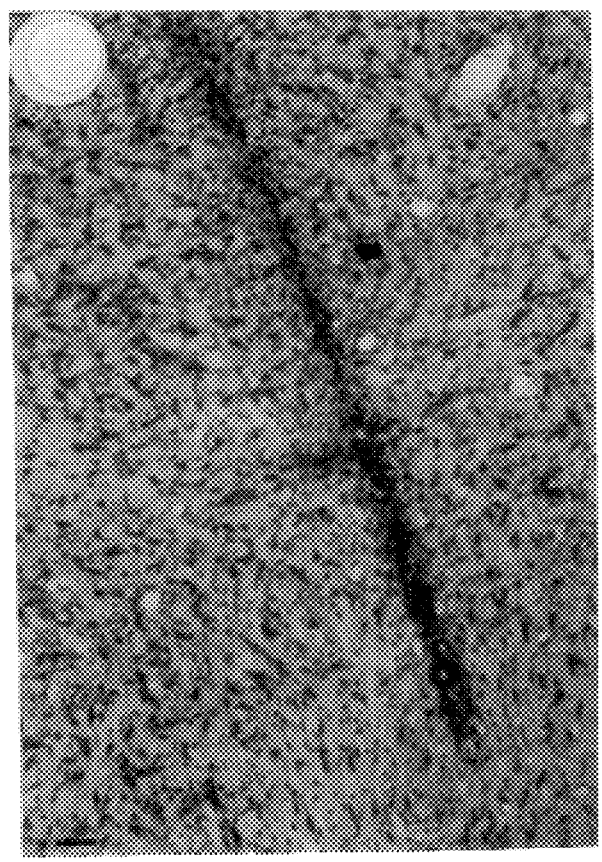
Figure 5D:
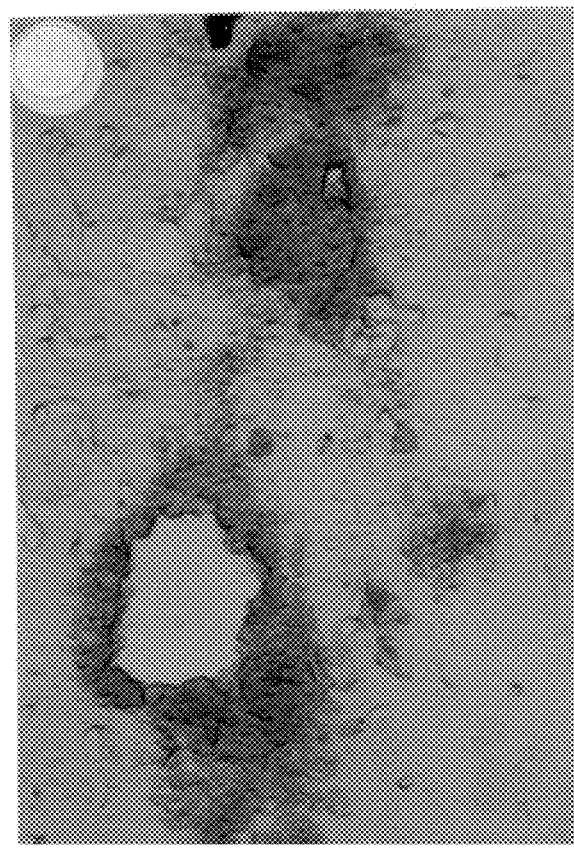
Figure 5E:
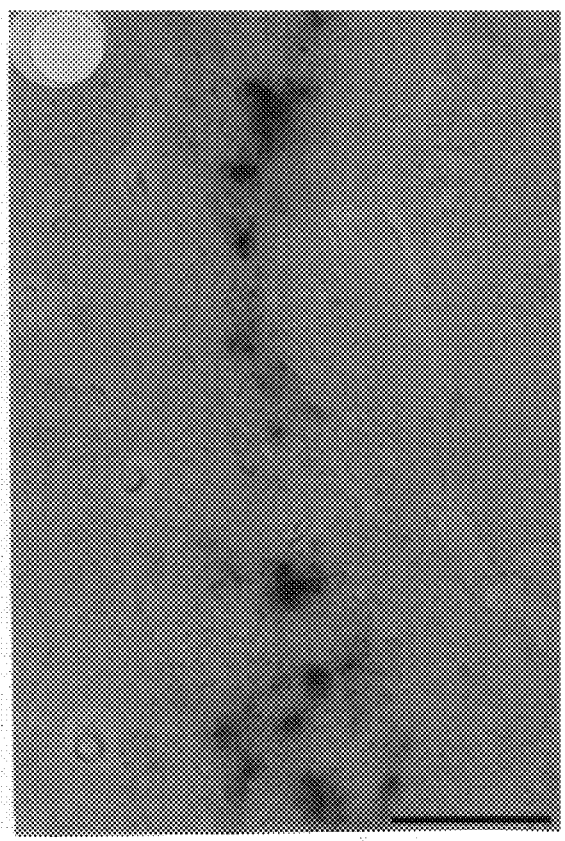
Figure 5F:
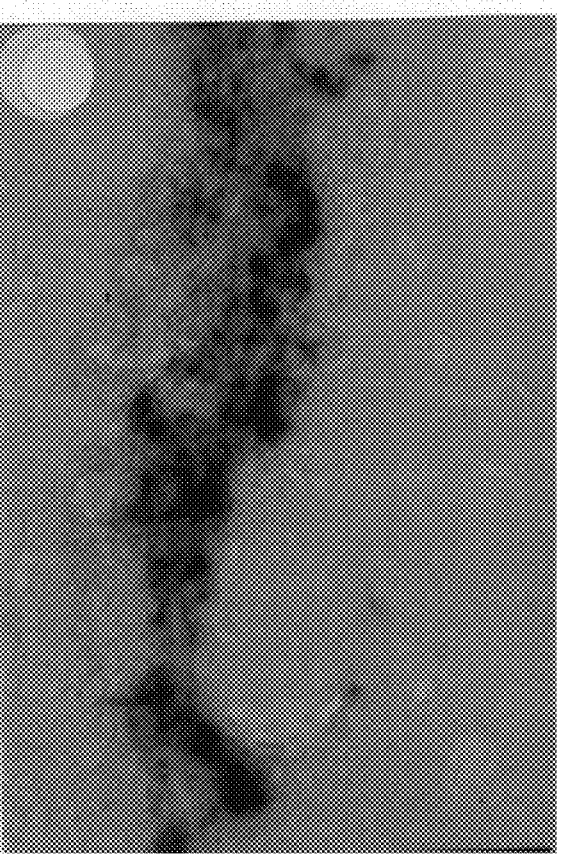
Figure 5G:
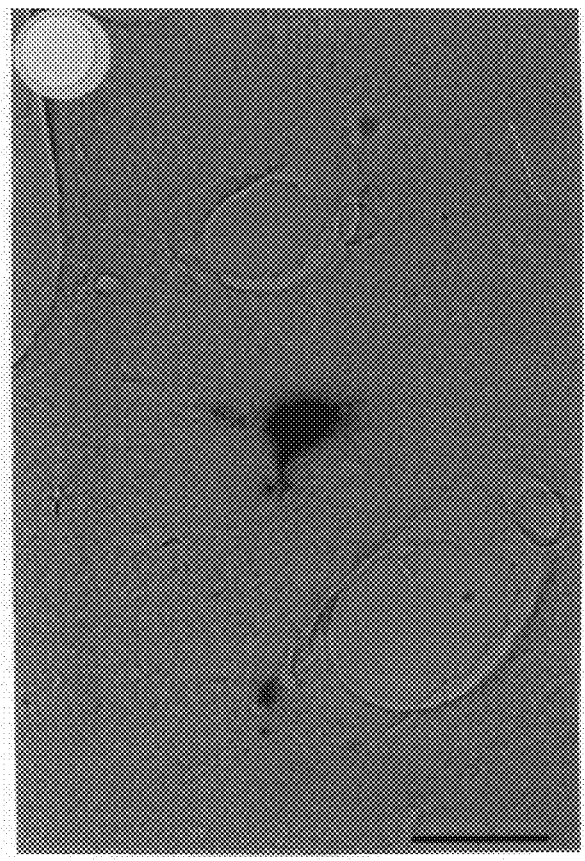
Figure 5H:
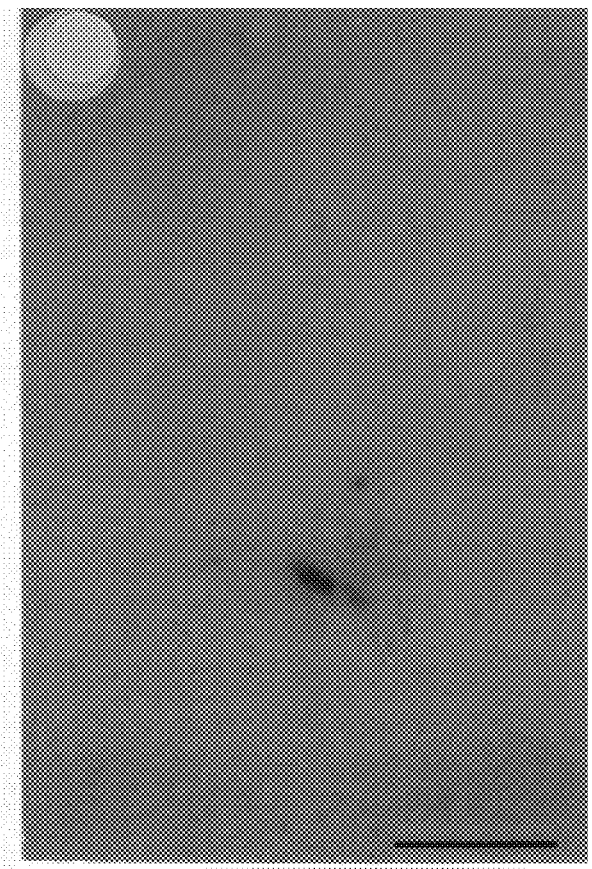

PCR demonstrated that pHSVlac DNA persisted for at least 1 month after injection of either pHSVlac/helper-free or pHSVlac/helper (FIG. 6), establishing that a helper virus is not required for persistence of pHSVlac DNA. All of the rats which received pHSVlac/helper-free appeared healthy, gained weight, exhibited unaltered ingestive and gross motor behaviors, survived until killed, and histological analysis revealed no brain tumors.

The absence of helper virus from these HSV-1 plasmid vector stocks resulted in (i) reduced probability for interactions with endogenous viruses, (ii) more efficient gene transfer, (iii) reduced cytopathic effects, and (iv) reduced cell infiltration. Many of these improvements may have been realized because gene expression from the helper virus was responsible for the majority of both the cytopathic effects and the immune response (Johnson, et al., (1992a); Johnson, et al., (1992b); Nguyen, et al., (1992); Johnson, et al., (1994); Wood, et al., (1994); Ho, et al., (1995)). Since vector DNA can persist in neural cells, inactivation of the IE 4/5 promoter is a likely explanation for at least a fraction of the instability in long-term gene expression in vivo, and increased stability might be achieved by using a different promoter. Additional modifications to the vector system may reduce potential remaining cytopathic effects and add additional barriers to the formation of HSV-1.

The following is a listing of publications referred to in the foregoing specification, the disclosures of which are incorporated herein by reference.

Ace, C I, Dalrymple, M A, Ramsay, F H Preston, V G, Preson, C M *J. Gen. Virol.* 69, 2595–2605, (1988);

Ace, C I, McKee, T A, Ryan, J M, Camerson, J M, Preston, C M *J. Virol.* 63, 2260–2269 (1989);

S. Akli et al., *Nat. Genet.* 3, 224 (1993);

Baines, J D, Roizman, B., *J. Virol.*, 65, 938–944, (1991);

Balan, P, Davis-Poynter, N, Bell, S. Atkinson, H, Browne, H. Minson, T., *J. Gen. Virol.,* (1994);

D. S. Battleman, A. I. Geller, M. V. Chao, *J. Neurosci.* 13, 941 (1993);

P. J. Bergold, P. Casaccia-Bonnefil, Z. Xiu-Liu, H. J. Federoff, *Proc. Natl. Acad. Sci. U.S.A.* 90, 6165 (1993);

Bobo, R H, Laske, D W, Akbasak, A, Morrison, P F, Dedrick, R L Oldfield, E H., *Proc. Natl. Acad. Sci.* 91, 2076–2080, (1994);

Carpenter, D E, Misra, V., *J. Gen. Virol.* 72, 3077–3084, (1991);

E. A. Chiocca et al., *N. Biol.* 2, 739 (1990);

D. W. Choi, M. Maulucci-Gedde, A. R. Kriegstein, *J. Neurosci.* 7, 357 (1987);

J. I. Cohen and K. E. Seidel, *Proc. Natl. Acad. Sci. U.S.A.* 90, 7376 (1993);

Coulter, L J, Moss, M W M, Lang, J. McGeoch, D J *J. Gen. Virol.*, 74, 387–395, (1993);

Cunningham, C, Davison, A J, Dolan, A, Frame, M C, McGeoch, D J, Meredith, D M, Moss, M W M, Orr, A C *J. Gen. Virol.*, 73, 303–311, (1992);

C. Cunningham and A. J. Davison, *Virology* 197, 116 (1993);

B. L. Davidson, E. D. Allen, K. F. Kozarsky, J. M. Wilson, B. J. Roessler, *Nat. Genet.* 3, 219 (1993);

A. T. Dobson, T. P. Margolis, F. Sedaerati, J. G. Stevens, L. T. Feldman, *Neuron* 5, 353 (1990);

M. J. During, J. Naegele, K. O'Malley, A. I. Geller, *Science* 266, 1399 (1994);

P. C. Emson et al., *Exp. Brain Res.* 79, 427 (1990);

Evans, et al., *Gene* 79, 9–20 (1989);

R. D. Everett, A. Cross, A. Orr., *Virology* 19 7151 (1993)

H. J. Federoff, M. D. Geschwind, A. I. Geller, J. A. Kessler, *Proc. Natl. Acad. Sci. U.S.A.* 89, 1636 (1992);

Ferrin, L J, Camerini-Otero, R D *Science* 254, 1494–1497, (1991);

D. J. Fink et al., *Hum. Gene Therapy* 3, 11 (1992);

Forss-Petter, et al., *Journal of Neuroscience Research* 16(1), 141–156 (1986);

Frank, et al., *Journal of Virology* 63(11), 4479–4488 (1989);

A. I. Geller and X. O. Breakefield, *Science* 241, 1667 (1988);

A. I. Geller and A. Freese, *Proc. Natl. Acad. Sci. U.S.A.* 87, 1149 (1990);

A. I. Geller, K. Keyomarski, J. Bryan, A. B. Pardee, *Proc. Natl. Acad. Sci. U.S.A.* 87, 8950 (1990);

A. I. Geller, M. J. During, J. W. Haycock, A. Freese, R. L. Neve, *Proc. Natl. Acad. Sci. U.S.A.* 90, 7603 (1993);

A. I. Geller, A. Freese, M. J. During, K. L. O'Malley, J. Neurochem. 64, 487 (1995);

M. D. Geschwind, J. A. Kessler, A. I. Geller, H. J. Federoff, *Mol. Brain Res.* 24, 327 (1994);

Green, et al., *Ann. Rev. Biochem.* 55:569–597, (1986)

C. L. Halbert, I. E. Alexander, G. M. Wolgamot, A. D. Miller, *J. Virol.* 69, 1473 (1995);

T. C. Heineman and J. I. Cohen, *J. Virol.* 68, 3317–3323 (1994);

Hidaka, Y., Sakuma, S., Kumano, U., Minagawa, H., and Mori, R., *Arch. Virol.,* 113, 195–207, (1990);

R. Higushi, *Amplifications* 2, 1 (1989);

D. Y. Ho, E. S. Mocarski, R. M. Sapolsky, *Proc. Natl. Acad. Sci. U.S.A.* 90, 3655 (1993);

D. Y. Ho and E. S. Mocarski, *Virology* 167, 279 (1988);

D. Y. Ho et al., *J. Neurosc. Meth.* 57, 205 (1995);

A. Kalnin, K. Otto, U. Ruether, B. Mueller-Hill, *Embo J.* 2:593 (1983);

M. G. Kaplitt et. al., *Nat. Genet* 8, 148 (1994);

J. Y. Koh and D. W. Choi, *J. Neurosci. Meth.* 20, 83 (1987);

P. A. Johnson, A. Miyanohara, F. Levine, T. Cahill, T. Friedmann, *J. Virol.* 66, 2952 (1992a);

P. A. Johnson, K. Yoshida, F. H. Gage, T. Friedmann, *Mol. Brain Res.* 12, 95 (1992b);

P. A. Johnson, M. J. Wang, T. Friedmann, *J. Virol.* 68, 6347 (1994);

Jones, et al., *J. Virol.* 69: 4863 (1989);

A. D. Kwong and N. Frenkel, *Virology* 142, 421 (1985);

G. Le Gal La Salle et al., *Science* 259, 988 (1993);

Lieb and Olivo *BioAssay*, 15, 547 (1995);

F. Lim et. al., in *DNA Cloning: Mammalian Systems*, D. Glover, Ed. (Oxford Univ. Press, Oxford England, 1995), in press;

MacLean, C A, Efstathiou, S. Elliott, M L, Jamieson, F E, McGeoch, D J, *J. Gen. Virol.*, 72, 897–906, (1991);

MacLean, C A, Robertson, L M, Jamieson, F E *J. Gen. Virol.*, 74, 975–983, (1993);

D. J. McGeoch et. al., *J. Gen. Virol.* 69, 1531 (1988);

McKnight, et al., *Journal of Virology* 61(4), 992–1001 (1987);

Morrison, P. F., Laske, D. W., Bobo, H., Oldfield, E. H., Dedrick, R. L., *Am. J. Physiol.* 266, 292–305, (1994)

L. H. Nguyen, D. M. Knipe, R. W. Finberg, *J. Virol.* 66, 7067 (1992);

O'Conner, et al., *Science* 244:1307–1313 (1989);

G. Paxinos, C. Watson, *The Rat Brain in Stereotaxic Coordinates* (Academic Press, (1986));

Pellegrino, L. J., and Cushman, A. J. *Methods in Psychobiology*, (Academic Press, New York, N.Y.) pp. 67–90 (1971);

Read, G S, Karr, B M, Knight, K, *J. Virol.*, 67, 7149–7160, (1993);

B. Roizman and F. J. Jenkins, *Science* 229, 1208 (1985);

Rossi, et al., *Pharmacol, Ther.* 50(2):245–354, (1991);

Sambrook, J. et al., *MOLECULAR CLONING: A LABORATORY MANUAL*, 2nd Edition, Cold Spring Harbor Press, Cold Spring Harbor, N.Y. (1989);

W. R. Sacks and P. A. Schaffer, *J. Virol.* 61, 829 (1987);

J. D. Schrag, B. V. V. Prasad, F. J. Rixon, W. Chiu, *Cell* 56, 651 (1989);

R. L. Smith, A. I. Geller, K. W. Escudero, C. L. Wilcox, *J. Virol., (*1995), in press;

I. L. Smith, M. A. Hardwick, R. M. Sandri-Goldin, *Virology* 186, 74 (1992);

Song, S., Wang, Y., Bak, S. Y., Lang, P., Ullrey, D., Neve, R. L., O'Malley, K. L., & Geller, A. I., A HSV-1 vector containing the rat tyrosine hydroxylase promoters directs long-term cell type specific expression in the midbrain (In preparation) (1995);

R. R. Spaete and N. Frenkel, *Cell* 30, 285 (1982);

P. G. Spear and B. Roizman, in *DNA Tumor Viruses*, J. Tooze, Ed. (Cold Spring Harbor Laboratories, New York, 1981) pp. 615–746;

J. G. Stevens, *Curr. Top. Microbiol. Immunol.* 70, 31 (1975);

B. Tomkinson, E. Robertson, R. Yalamanchili, R. Longnecker, E. Kieff, *J. Virol.* 67, 7298 (1993);

M. van Zijl et al., *J. Virol.* 62, 2191 (1988);

Rosen-Wolff, A, Lamade, W. Berkowitz, C. Bekcer, Y. Darai, G., *Virus Research* 20, 205–221, (1991);

J. H. Wolfe, S. L. Deshmane, N. W. Fraser, *Nat. Genet.* 1, 372 (1992);

M. J. A. Wood, A. P. Byrnes, D. W. Pfaff, S. D. Rabkin, H. M. Charlton, *Gene Therapy* 1, 283 (1994);

H. Xu, H. Federoff, J. Maragos, L. F. Parada, J. A. Kessler, *Devel. Biol.* 163, 152 (1994);

Y. Yang et al., *Proc. Natl. Acad. Sci. U.S.A.* 91, 4407 (1994);

Y. Yang, Q. Li, H. C. J. Ertl, J. M. Wilson, *J. Virol.* 69, 2004 (1995).

It is evident that those skilled in the art, given the benefit of the foregoing disclosure, may make numerous modifications thereof and departures from the specific embodiments described without departing from the inventive concepts and the present invention is to be limited solely by the scope and spirit of the appended claims.

What is claimed is:

1. A method for delivery of a heterologous DNA to a target cell comprising contacting said target cell with or administering to a host containing said target cell, a herpesvirus particle containing said heterologous DNA sequence,5 wherein said herpesvirus particle is formed from vectors wherein (a) DNA segments encoding structural herpesvirus proteins lack a functional herpesvirus cleavage/packaging site-containing sequence, and (b) the heterologus DNA sequence was present in a vector containing a herpesvirus packaging site-containing sequence, and an origin of DNA replication recognized by the herpesvirus DNA replication proteins and enzymes, and wherein a promoter sequence was operably linked to the heterologus sequence and at least one sequence sufficient to permit transcription and processing of an RNA.

2. The method of claim 1, wherein the target cell is a dividing cell or a quiscent cell.

3. The method of claim 2, wherein the quiscent cell is a nonmitotic cell or a postmitotic cell.

4. The method of claim 3, wherein the nonmitotic cell is a glia and the postmitotic cell is a neuron.

5. The method of claim 1, wherein the target cell is a cell type of the nervous system.

6. The method of claim 5, wherein the target is a neural or neuronal cell.

7. The method of claim 1, wherein the structural herpesvirus proteins are from an alpha herpesvirus and the herpesvirus packaging site-containing sequence are from an alpha herpesvirus.

8. The method of claim 1, wherein the structural herpesvirus proteins are from a herpes simplex virus, and the herpesvirus packaging site-containing sequences are from a herpes simplex virus.

9. The method of claim 8, wherein the herpes simplex virus is herpes simplex type-1 or herpes simplex type-2.

* * * * *